(12) United States Patent
Baksh (10) Patent No.: US 8,846,082 B2
(45) Date of Patent: *Sep. 30, 2014

(54) PROBIOTIC AND PRESERVATIVE USES OF OIL-EMULSIFIED PROBIOTIC ENCAPSULATIONS

(75) Inventor: Bing Baksh, Placentia, CA (US)

(73) Assignee: Vita-Herb Nutriceuticals, Inc., Placentia, CA (US)

( * ) Notice: Subject to any disclaimer, the term of this patent is extended or adjusted under 35 U.S.C. 154(b) by 995 days.

This patent is subject to a terminal disclaimer.

(21) Appl. No.: 11/386,159

(22) Filed: Mar. 21, 2006

(65) Prior Publication Data

US 2006/0159745 A1    Jul. 20, 2006

Related U.S. Application Data

(62) Division of application No. 10/672,668, filed on Sep. 26, 2003, now Pat. No. 7,214,370.

(60) Provisional application No. 60/414,083, filed on Sep. 26, 2002.

(51) Int. Cl.
| | | |
|---|---|---|
| *A61K 9/48* | (2006.01) | |
| *A61K 38/44* | (2006.01) | |
| *A01N 63/00* | (2006.01) | |
| *C12N 1/12* | (2006.01) | |
| *C12N 1/20* | (2006.01) | |
| *C12P 1/04* | (2006.01) | |
| *A23L 1/30* | (2006.01) | |

(52) U.S. Cl.
CPC ............. *A23L 1/3014* (2013.01); *A61K 9/4833* (2013.01); *A23V 2002/00* (2013.01); *A23Y 2220/17* (2013.01); *Y10S 435/822* (2013.01); *Y10S 435/856* (2013.01)
USPC ....... 424/454; 424/93.4; 424/93.45; 435/170; 435/252.1; 435/822; 435/856

(58) Field of Classification Search
None
See application file for complete search history.

(56) References Cited

U.S. PATENT DOCUMENTS

| | | | | |
|---|---|---|---|---|
| 3,071,513 | A | * | 1/1963 | De Boer et al. ............... 424/454 |
| 4,250,997 | A | * | 2/1981 | Bodenmann et al. ......... 206/528 |
| 4,539,060 | A | | 9/1985 | Wittwer et al. |
| 6,797,266 | B2 | * | 9/2004 | Naidu ......................... 424/93.45 |
| 2002/0081330 | A1 | * | 6/2002 | Young .......................... 424/451 |

* cited by examiner

*Primary Examiner* — Debbie K Ware
(74) *Attorney, Agent, or Firm* — Cotman IP Law Group, PLC (57) ABSTRACT

An encapsulation system is provided comprising nitrogen-purge, instant bonding encapsulation method. Specifically, the encapsulation system comprises a composition, a two-piece capsule comprising a capsule cap and a capsule body; a gas to purge oxygen from the composition within the capsule; and a sealing solution to seal the capsule cap to the capsule body. Associated methods for encapsulating compositions using the encapsulation system are also provided.

8 Claims, 4 Drawing Sheets

SEQUENCE LISTING

```
<160> NUMBER OF SEQ ID NOS: 2

<210> SEQ ID NO 1
<211> LENGTH: 20
<212> TYPE: DNA
<213> ORGANISM: Lactobacillus casei

<400> SEQUENCE: 1
ttgtcaccgg cagttcttac                                              20

<210> SEQ ID NO 2
<211> LENGTH: 19
<212> TYPE: DNA
<213> ORGANISM: Lactobacillus casei

<400> SEQUENCE: 2
tgtcgtcagc tcgtgtcgt                                               19
```

PROBIOTIC AND PRESERVATIVE USES OF OIL-EMULSIFIED PROBIOTIC ENCAPSULATIONS

RELATED APPLICATIONS

The present application is a division of U.S. patent application Ser. No. 10/672,668 filed Sep. 26, 2003, now U.S. Pat. No. 7,214,370, which claims priority to U.S. provisional patent application Ser. No. 60/414,083 filed Sep. 26, 2002, the contents of which are incorporated by reference herein in their entirety.

FIELD OF THE INVENTION

The present invention is directed at probiotic compositions and methods for making same. More specifically, the present invention is directed at probiotic compositions derived from lactic acid bacteria that have been emulsified in prebiotic edible oils and packaged in an anaerobic encapsulation system.

BACKGROUND OF THE INVENTION

Probiotics are microbial-based dietary adjuvants that beneficially affect the host physiology by modulating mucosal and systemic immunity, as well as improving nutritional and microbial balance in the intestinal tract [Naidu A S et al. Probiotic spectra of lactic acid bacteria (LAB). Crit. Rev. Food Sci. Nutr. 39:3-126, 1999]. Lactic acid bacteria (LAB) are indigenous probiotic microflora of mammalian gastrointestinal tract that play an important role in the host microecology and have been credited with an impressive list of therapeutic and prophylactic properties [Naidu A S, Clemens R A Probiotics, p. 431-462. In A S Naidu (ed.), Natural Food Antimicrobial Systems. CRC Press, Boca Raton, Fla., 2000]. These therapeutic and prophylactic properties include, but not limited to the maintenance of microbial ecology of the gut, physiological, immuno-modulatory and antimicrobial effects [Gibson G R et al., Probiotics and intestinal infections, p. 10-39. In R. Fuller (ed.), Probiotics 2: Applications and practical aspects. Chapman and Hall, London, UK, 1997]. Other LAB associated attributes include enzyme release into the intestinal lumen that act synergistic with LAB adhesion to alleviate symptoms of intestinal malabsorption. Furthermore, the LAB-released enzymes help regulate intestinal pH that results in increased aromatic amino acid degradation [Mitsuoka T Taxonomy and ecology of bifidobacteria. Bifidobacteria Microflora 3:11, 1984]. LAB have also demonstrated the ability to significantly reduce sulfide and ammonia containing compounds in animal fecal waste and thus reduce the odor and toxicity associated with animal excrements [Naidu A S et al., Reduction of sulfide, ammonia compounds and adhesion properties of *Lactobacillus casei* strain KE99 in vitro. Curr. Microbiol. 44:196-205, 2002].

However, the greatest potential for LAB to improve life quality for man and domestic animals lies in their in vivo probiotic applications. In order for LAB to exhibit beneficial probiotic effects in vivo, the organisms must survive for extended time periods in the gut. Therefore, it is critical that probiotic LAB strains be selected that possess qualities that prevent their rapid removal by gut contraction [Havenaar R et al., Selection of strains for probiotic use, p. 209-224. In R. Fuller (ed.), Probiotics, the scientific basis. Chapman and Hall, London, UK, 1992]. Effective probiotic bacteria should be able to survive gastric conditions and colonize the intestine, at least temporarily, by adhering to the intestinal epithelia [Conway P. Selection criteria for probiotic microorganisms. Asia Pacific J. Clin. Nutr 5:10-14, 1996].

Furthermore, in addition to increasing in vivo viability and gastrointestinal tract life span, prolonged shelf life at room temperature remains a commercial challenge. Lactic acid bacilli generally require an effective delivery system that retains probio-functional activities (i.e. gut adhesion/retention, production of bacteriocins/enzymes) after their revival [Salminen S et al., Clinical uses of probiotics for stabilizing the gut mucosal barrier: successful strains and future challenges. Antonie Van Leeuwenhoek 70:347-3581, 1996]. Though freeze-drying is an effective process for preservation and delivery of probiotics, several physico-chemical factors such as humidity, aeration (oxygen availability) and temperature could compromise the cell viability, thereby the shelf life.

One potential additive class that may increase both in vivo life span and storage shelf-life is prebiotics. Prebiotics are non-digestible, or partially digestible, food ingredients that beneficially affect the host by selectively simulating the growth and/or activity of one or a limited number of bacterial species and thus in effect improve host health. [Gibson G R, Roberfroid M B. Dietary modulation of the human colonic microbiota: Introducing the concept of prebiotics. J. Nutr. 125:1401-12, 1995]. Intake of prebiotics can beneficially modulate probiotic LAB. Non-digestible oligosaccharides such as dietary fiber in general, and fructo-oligosaccharides (FOS) in particular, are well known prebiotics [Roberfroid M B. Health benefits of non-digestible oligosaccharides. Adv. Exp. Med. Biol. 427:211-9, 1997]. By combining the rationale of probiotics and prebiotics, the concept of 'synbiotics' is proposed to characterize some colonic foods with interesting nutritional properties in combination with health-enhancing functional food ingredients [Fuller R, Gibson G R Modification of the intestinal microflora using probiotics and prebiotics. Scand. J. Gastroenterol. Suppl. 222:28-31,1997].

Essential oils are known as biological preservatives due to their low water activity and limited air diffusion. Several essential oils also known to provide various nutraceutical benefits including antioxidant, antimicrobial, antitumor, and immune-modulatory activities. However, the prebiotic effects of essential oils on probiotic LAB are heretofore unknown. Therefore, there remains a need to enhance probiotic activity, in vivo viability and shelf life of probiotic compositions including LAB. One potential solution is the application of prebiotics in combination with advanced packaging methods.

SUMMARY OF THE INVENTION

It is an object of the present invention to provide enhanced probiotic compositions having increased viability, in vivo life span and increased shelf life.

It is another object of the present invention to provide a prebiotic composition in combination with a new strain of *lactobacillus* having increased viability, in vivo life span and increased shelf life.

It is yet another object of the present invention to preserve the probiotic qualities of *Lactobacillus casei* KE01 including, but are not limited the use of the prebiotic oil compositions of the present invention in combination with by an encapsulation process using a novel Nitrogen-Purge, Instant-Bonding (NPIB) system.

The present invention fulfills these and other objects by providing a new strain of *Lactobacillus casei* designated KE01 that possesses scientifically proven probiotic properties including demonstrated in vivo anti-enteric pathogen activity. Moreover, the present invention provides dietary supplements and pharmaceutical preparations composed of *L. casei* strain KE01 that are formulated in a prebiotic composition of edible oils that provided long term protection to the organism and help maintain its proven probiotic properties and increased in vivo life span and shelf life.

There is a need for new probiotic formulations that can be used to treat and prevent enteric-pathogen infections and help maintain the health and vitality of humans and livestock. Recently, the Federal Food and Drug Administration (FDA) has intensified its campaign against the over prescription and clinical abuse of antibiotics. The excessive use of antibiotics has increased in the number of human and animal pathogens that are resistant to first-line antibiotics resulting in an increase in infections that do not respond to conventional antimicrobial therapies. Moreover, the prophylactic use of antibiotics in animal feed has resulted in an alarming increase in livestock intestinal infections resulting in diminished herd size and animal weight due to nutrient malabsorption. Consequently, the number of healthy animals suitable for human consumption has dropped, and those that do survive long enough to reach market have significantly lower weights and consequently reduced meat quality.

One means of preventing the rapid spread of drug resistant enteric pathogens in humans and livestock is to significantly reduce antibiotic use. However, the spread of communicable diseases including enteric infections is inevitable due to over crowding of farms and cities. Consequently, before prophylactic antibiotic use can be completely discontinued a suitable antimicrobial alternative must be available. Recent studies have indicated that the use of foodstuffs and dietary supplements containing specific strains of probiotic microorganisms can help prevent, and in many cases actually cure, enteric pathogen diseases. However, many of the probiotic formulas currently marketed rely on organisms including *Lactobacillus* spp and *Bifidobacteria* sp (and other genera) that have not been subjected to scientific scrutiny using approved methods for assessing probiotic efficacy. Consequently, too many of the "probiotic" formulas currently available lack proven in vivo anti-enteric pathogen activity. Moreover, many of the clinically effective probiotic formulations commercially available are not stable upon storage and therefore do not deliver effective amounts of viable probiotic bacteria to the user. The present inventors have tested many commercially available preparations and found microbial viability well below stated concentrations and in many cases the present inventor has found that these commercial preparations did not contain any viable bacteria.

The present inventors have developed methods for preparing and packaging a new strain of *L. casei*, designated KE01. This new strain of *L. casei* was originally from a traditional fermented yogurt-like Asian dairy product by the present inventor. Subsequently, the present inventor characterized the isolate and the strain deposited with the American Type Culture Collection (ATCC, MD, USA)). *Lactobacillus casei* strain KE01 has been given the ATCC depository number PTA 3945. Moreover, the present inventors have developed preparations and packaging systems that maintain *L. casei* KE01 viability such that a clinically effective dose of viable probiotic microorganisms reaches the host.

The present invention provides a *L. casei* strain (KE01) that interferes with bacterial adherence (microbial interference) of enteric pathogens such as, but not limited to enteropathogenic and enterotoxigenic *E. coli*, *Helicobacter pylori*, *Campylobacter jejuni*, *S. typhimurium*, and *S. enteritidis* to a variety of mammalian cell types. Moreover, the *Lactobacillus* of the present invention can also competitively exclude (competitive exclusion) these, and other bacterial pathogens, from binding to many mammalian cells. The beneficial properties associated with the novel *Lactobacillus* strain of the present invention have resulted in improved probiotic dietary supplements that support general human and animal health. Moreover, the present invention can be used to provide prophylactics, therapeutics and palliatives (collectively referred to herein as "probiotics") for conditions such as, but not limited to, traveler's diarrhea, gastrointestinal infections, hemolytic uremic syndrome, and gastric ulcers.

Additional novel features and qualities of this new *L. casei* strain KE01 include, but are not limited to, *L. casei* KE01's ability to reduce sulfide concentrations by a factor exceeding 300 ppm within 48 hours when exposed to a growth medium containing approximately 2000 ppm of sulfides and the demonstration of avid binding to sub-epithelial matrices including Bio-coat™ (Collagen type-I, Collagen type IV, laminin, and fibronectin), Matrigel™ and Caco-2 cell monolayers. Most importantly, a reconstituted, freeze-dried preparation of the *L. casei* of the present invention has been shown to effectively detach collagen-adherent *E. coli*.

The methods used to maintain the viability of the *L. casei* of the present invention and preserve probiotic qualities include, but are not limited the use of the prebiotic oil compositions of the present invention in combination with by an anaerobic encapsulation process using a novel Nitrogen-Purge, Instant-Bonding (NPIB) system.

These and other beneficial probiotic properties of the new strain of *Lactobacillus* will be further evident by the following, non-limiting, detailed description of the present invention.

DETAILED DESCRIPTION OF THE INVENTION

Lactic acid bacteria (LAB) are indigenous microflora of mammalian gastrointestinal tract that play an important role in the host microecology and have been credited with an impressive list of therapeutic and prophylactic properties. These therapeutic and prophylactic properties include, but not limited to the maintenance of microbial ecology of the gut, physiological, immuno-modulatory and antimicrobial effects. Other LAB associated attributes include enzyme release into the intestinal lumen that act synergistically with LAB adhesion to alleviate symptoms of intestinal malabsorption. Furthermore, the LAB enzymes help regulate intestinal pH which results in increased aromatic amino acid degradation. [Fuller R. Probiotic foods—current use and future developments. IFI NR 3:23-6, 1993; Mitsuoka T Taxonomy and ecology of Bifidobacteria. Bifidobacteria Microflora 3:11, 1984; Gibson G R et al., Probiotics and intestinal infections, p. 10-39. In R. Fuller (ed.), Probiotics 2: Applications and practical aspects. Chapman and Hall, London, U.K. 1997; Naidu A S et al., Probiotic spectra of lactic acid bacteria (LAB). Crit Rev Food Sci Nutr 39:3-126. 1999; Naidu A S, Clemens R A. Probiotics, p. 431-462. In A S Naidu (ed.), Natural Food Antimicrobial Systems. CRC Press, Boca Raton, Fla., 2000].

Lactic acid bacteria have also demonstrated the ability to significantly reduce sulfide and ammonia containing compounds in animal fecal waste and thus reduce the odor and toxicity associated with animal excrements. This ex vivo LAB application is becoming increasingly more important as agro-businesses expand and as communities continue their seemingly never ending encroachment into previously unoccupied rural areas. For example, LAB has been demonstrated to eliminate offensive odors and reduce hydrogen sulfide production associated with hatchery waste when cockerel chicks and shell waste are blended with a mixture containing 15% carbohydrate and LAB. Moreover, LAB compositions have demonstrated efficacy in diminishing the *Escherichia coli* and *Salmonella* content of hatchery waste to negligible levels.

Additionally, the odor and viscosity of poultry offals such as broiler-processing waste is significantly reduced by *L. acidophilus* mediated lactic acid fermentation. Furthermore, preparations containing LAB have been reported to accelerate the breakdown of hard-to-degrade carbohydrates and decrease the ammonia production by porcine cecal bacteria. Finally, ex vivo *L. casei* FG1 and *L. plantarum* silage fermentation significantly reduces ammonia levels by inhibiting urea-splitting organisms. [Deshmukh A C, Patterson P H. Preservation of hatchery wastes by lactic acid fermentation. 1. Laboratory scale fermentation. Poult Sci 76:1212-19, 1997; Russell S M et al., Lactic acid fermentation of broiler processing waste: physical properties and chemical analyses. Poult Sci 71:765-70, 1992; Tibbetts G W et al., Poultry offal ensiled with *Lactobacillus acidophilus* for growing and finishing swine diets. J Anim Sci 64:182-90, 1987; Sakata T et al., Probiotic preparations dose-dependently increase net production rates of organic acids and decrease that of ammonia by pig cecal bacteria in batch culture. Dig Dis Sci 44:1485-93, 1999; Cai Y et al., Effect of applying lactic acid bacteria isolated from forage crops on fermentation characteristics, aerobic deterioration of silage. J Dairy Sci 82:520-6, 1999; Modler H W et al., Bifidobacteria and bifidogenic factors. Can Inst Food Sci Tech 23:29-41,1990].

However, the greatest potential for LAB to improve life quality for man and domestic animals lies in LAB in vivo probiotic applications. In order for LAB to exhibit beneficial probiotic effects in vivo, the organisms must survive for extended time periods in the gastrointestinal tract. Therefore, it is critical that probiotic LAB strains be selected that possess qualities that prevent their rapid removal by gut contraction. Effective probiotic bacteria must able to survive gastric conditions and colonize the intestine, at least temporarily, by adhering to the intestinal epithelium. Consequently, LAB that demonstrate an enhanced ability to adhere to mucosal surfaces, and therefore possess improved bacterial maintenance and prolonged gastrointestinal tract residence times, have a competitive advantage over LAB that do not. [Salminen S et al., Clinical uses of probiotics for stabilizing the gut mucosal barrier: successful strains and future challenges. Antonie Van Leeuwenhoek 70:347-58, 1996; Conway P. Selection criteria for probiotic microorganisms. Asia Pacific J Clin Nutr 5:10-14, 1996; Havenaar R et al., Selection of strains for probiotic use, p. 209-224. In R. Fuller (ed.), Probiotics, the scientific basis. Chapman and Hall, London, U.K., 1992].

*Lactobacillus* can successfully colonize the mammalian gastrointestinal tract through a number of different mechanisms. For example, some bacterial species bind to various sub-epithelial matrix proteins and specific receptors on the intestinal mucosa. Other species may adhere to mammalian intestinal cells via mechanisms that involve different combinations of carbohydrate and protein factors on the bacteria and host eukaryotic cell surfaces. However, regardless of the mechanism(s) of attachment, it is the ability of LAB to successfully colonize the human gastrointestinal tract that provides LAB with probiotic qualities. [Greene J D, Klaenhammer T R Factors involved in adherence of *lactobacilli* to human Caco-2 cells. Appl Environ Microbiol 60:4487-94, 1994; Sarem F et al., Comparison of the adherence of three *Lactobacillus* strains to Caco-2 and Int-407 human intestinal cell lines. Lett Appl Microbiol 22:439-42, 1996; Naidu A S et al., Particle agglutination assays for rapid detection of fibronectin, fibrinogen, and collagen receptors on *Staphylococcus aureus*. J Clin Microbiol 26:1549-54, 1988; Wadstrom T et al., Surface properties of *lactobacilli* isolated from the small intestines of pigs. J Appl Bacteriol 62:513-20, 1987; Bernet M F et al., *Lactobacillus acidophilus* LA 1 binds to cultured human intestinal cell lines and inhibits cell attachment, invasion by entero-virulent bacteria. Gut 35:483-9, 1994; Jin L Z et al., Effect of adherent *Lactobacillus* spp. on in vitro adherence of salmonellae to the intestinal epithelial cells of chicken. J Appl Bacteriol 81:201-6, 1996; Reid G et al., Influence of *lactobacilli* on the adhesion of *Staphylococcus aureus* and *Candida albicans* to fibers and epithelial cells. J Ind Microbiol 15:248-53, 1995].

Generally speaking probiotic bacteria exert their beneficial effects by displacing invasive or toxigenic pathogenic enteric bacteria (enteric pathogens) from the intestinal mucosa through a competitive binding process. Enteric pathogens such as, but not limited to, enteropathogenic *Escherichia coli* (EPEC), enterotoxigeneic *E. coli* (ETEC), *Salmonella enteriditis*, *Yersina pseudotuberculosis* and *Listeria monocytogenes* must be able to successively colonize an animal's intestinal tract in order to cause disease.

Probiotic compositions exert optimal beneficial qualities when the percentage of viable probiotic bacteria is high. However, maintaining bacteria viability constitutes a significant challenge to the probiotic industry. Consequently, most probiotic compositions have a relatively short shelf life or are used with percent viabilities that are suboptimal. Many probiotic compositions, including those of the present invention are made using selected stains of (or combination of) bacteria including *Lactobacillus acidophilus*, *L. amylovorus*, *L. brevis*, *L. bulgaricus*, *L. casei* spp. casei, *L. casei* spp. *rhamnosus*, *L. crispatus*, *L. delbrueckii* ssp. *lactis*, *L. fermentum*, *L. helvaticus*, *L. johnsonii*, *L. paracasei*, *L. pentosus*, *L. plantarum*, *L. reuteri*, and *L. sake*: the genus *Bifidobacterium* including: *B. animalis*, *B. bifidum*, *B. breve*, *B. infantis*, and *B. longum*: the genus *Pediococcus* including: *P. acidilactici*: the genus *Propionibacterium* including: *P. acidipropionici*, *P. freudenreichii*, *P. jensenii*, and *P. theonii*: and the genus *Streptococcus* including: *S. cremoris*, *S. lactis*, and *S. thermophilus* (collectively referred to herein after as lactic acid bacteria, or LAB).

Presently, probiotic compositions are produced using cultured, concentrated LAB that are dried or lyophilized and then mixed with stabilizing ingredients such proteins and sugars including, but not limited raffinose, soybean oligosaccharides, fructooligosaccharides, galactooligosaccharides, galactosyl lactose and palatinose, lactulose, lactitol, xylitol, sorbitol, mannitol, trehalose, glucose, sucrose, fructose, maltose, milk, milk powders, whey, whey protein concentrates, casein, casein hydrolysates, lactoferrin, lactoperoxidase, lactoglobulins, glycomacropeptides, lacto-saccharides, and lacto-lipids. These probiotic mixtures are milled into small granule or fine powders and then sealed in various pharmaceutically acceptable forms and packaged. Alternatively, liquid preparations are provided that must be stored at refrigerator temperatures. However, regardless of the form, whether dried or liquid, LAB viability begins to drop dramatically soon after shipping to retail outlets and end users.

The present inventors have surprisingly discovered that certain edible oils not only protect LAB viability better than prior art stabilizing ingredients such proteins and sugars, actually enhance viability resulting in a prebiotic effect. As previously discussed, prebiotics are non- or partially digestible food ingredients that beneficially affect the host by selectively simulating the growth and/or activity of one or a limited number of bacterial species in the colon, and thus in effect improve host health. One embodiment of the present invention is a dietary supplement comprising approximately from $10^5$ to $10^{11}$ colony forming units of viable LAB per mL of prebiotic edible oil. However, it is understood that the probiotic compositions of the present invention are not limited by this range and may in fact comprises from approximately 1 to >$10^{12}$ colony forming units of viable *lactobacilli* per mL of prebiotic edible oil.

In one embodiment of the present invention the LAB *Lactobacillus casei* strain KE01 having the American Type Culture Collection (ATCC) accession number PTA 3945. In one embodiment of the present invention the prebiotic/probiotic composition comprises a hard two piece capsule filled with a *lactobacillus* composition suspended in at least one edible oil. In this embodiment the hard two piece capsule has been purged with an inert gas upon filling and sealed to assure an oxygen-free environment, as described more fully below. The hard two piece capsule can be derived from either vegetables, animal gelatin or synthetic and natural polymers.

Throughout this specification the present invention may be referred to as a probiotic composition, a *lactobacillus* containing composition, a dietary supplement, or a probiotic/prebiotic composition. All of these aforementioned terms mean a composition, regardless of form or the presence or absence of other ingredients, that contains viable and orl non-viable LAB and at least one prebiotic, edible oil. In one embodiment the LAB is *Lactobacillus casei* strain KE01 having ATCC accession number PTA 3945 or it genetic equivalent as determined using the methods detailed herein.

In one embodiment of the present invention an animal is provided with a single dose containing from approximately $10^5$ to $10^{11}$ *lactobacilli* per gram of probiotic composition. The total amount consumed will depend on the individual needs of the animal and the weight and size of the animal. The preferred dosage for any given application can be easily determined by titration. Titration is accomplished by preparing a series of standard weight doses each containing from approximately $10^5$ to $10^{11}$ *lactobacilli* per gram. A series of doses are administered beginning at 0.5 grams and continuing up to a logical endpoint determined by the size of the animal and the dose form. The appropriate dose is reached when the minimal amount of *lactobacilli* composition required to achieve the desired results is administered. The appropriate dose is also known to those skilled in the art as an "effective amount" of the probiotic compositions of the present invention.

For example, if it is desired to reduce the symptoms associated with irritable bowel syndrome in an animal, one measured dose as described above is administered daily, escalating the dose each successive day in 0.5 grams increments until symptoms subside. In one embodiment of the present invention the preferred dose is between approximately $10^3$ to $10^8$ viable *lactobacilli* per kilogram of body weight (the weight of the animal recipient) per day. This equates to approximately 10 billion viable LAB per day for the average healthy adult human. By extrapolation, it is a simple matter to calculate the approximate dose appropriate for any animal of any weight. It is understood that this is a non-limiting example that can be varied as appropriate by persons having skill in the art of prescribing probiotic compositions or by using the titration method provided above.

The probiotic compositions of the present invention can be administered to any animal in need of thereof including, but not limited to mammals, birds, reptiles and fish. Typical applications include administering the probiotic compositions of the present invention to humans, horses, swine (pigs), cows, sheep, dogs, cats, rabbits, chickens, turkeys, pheasants, quail, parakeets, parrots, and other wild and domesticated animals.

Specifically, the probiotic compositions of the present invention can be used to inhibit or treat enteric pathogen-associated diseases when administered to an animal in need thereof using the methods described in the present specification. Enteric pathogen diseases include those diseases caused by pathogens such as diarrhea, irritable bowel syndrome and intestinal hemorrhages. Examples of enteric pathogens associated with these diseases include, but not limited to enteropathogenic *Escherichia coli* (EPEC), enterotoxigeneic *E. coli* (ETEC), *Salmonella enteriditis, Yersina pseudotuberculosis* and *Listeria monocytogenes*. It is theorized by the present inventor, and not offered as a limitation, that the inhibition and treatment of the enteric pathogen diseases is accomplished by the probiotic composition of the present invention through a competitive binding process. That is, the probiotic *lactobacilli* of the present invention compete with enteric pathogens for binding sites on the intestinal mucosa. Because the probiotic *lactobacilli* of the present invention have a higher affinity and avidity for these binding sites than the enteric pathogens, the probiotic *lactobacilli* of the present invention displace the enteric pathogens into the intestinal milieu where they are harmlessly flushed from the intestines by normal metabolic processes.

In one embodiment of the present invention the probiotic organism of the present invention was isolated from a traditional fermented yogurt-like Asian dairy product. The screening process was limited to traditional fermented yogurt-like Asian dairy products with at least a ten-year history of safe human consumption. Probiotic bacteria isolation was performed using three selective microbiological media using methods known to those of ordinary skill in the art of microbiology. *Lactobacilli* selective media included SL medium supplemented with 0.05% cystein, *Bifidobacterium* spp. were selected for using trypticase peptone yeast extract medium containing antibiotics; and for *Streptococcus* spp. were isolated using trypticase yeast extract cystein medium.

Candidate probiotic *lactobacilli* were be catalase negative, glucose homofermentative, Gram-positive non-spore forming rods demonstrating low pH, gastric acid and bile resistance. The *lactobacilli* isolates' inability to grow at pH 9.0 coupled with their ability to grow on acetate containing media served to distinguish them from *Carnobacterium* spp. A total of 81 isolates were classified as candidate probiotic *lactobacilli* based on these criteria and were further characterized with respect to the following criteria: i) resistance to low pancreatic juice; ii) adherence ability to sub-epithelial matrices such as Biocoat™, Matrigel™ (Becton Dickinson, Bedford, Mass.) and to cultured intestinal epithelial cells (Caco-2 cell line); iii) their ability to competitively exclude enterohemorrhagic *E. coli* serotype O157:H7 adherent to collagen matrices; and iv) their capacity to reduce ammonia and sulfide containing compounds.

After analyzing all 81-candidate probiotic *lactobacilli*, two strains were identified having all of the above-identified characteristics. These strains were designated strain KE97 and strain KE99 (re-designated KE01). Finally the growth-multiplication rate (generation time as determined by impedance detection using BioMerieux™ Bactometer System), stability of strains in continuous culture, freeze-drying and revival characteristics, and aroma/flavor profiles were ascertained for each strain.

The isolated *Lactobacillus casei* strain KE01 organism is maintained in a substantially pure culture for use in preparing probiotic compositions of the present invention. As used herein "substantially pure culture" refers to a bacteriological culture that results in only one identifiable organism when cultured on solid or semi-solid microbiological culture media. It is understood that extremely low levels of cells from other bacterial species may be present; however, these cells are either non-viable, non-cultivable or below the threshold of detection using classical, non-genome-based, microbiological techniques. The term "non-genome-based" is intended to excluded such methods as PCR detection or similar methods used to detect microbial DNA or RNA.

Real-Time PCR (RT-PCR) for Specific Measurement of Strain KE01 for Quality (Purity) and Quantity (Total Bacterial Numbers)

In addition to estimating CFU counts by standard plate counts on MRS agar, RT-PCR assay was used for qualitative/quantitative measurement of survival and revival rates of strain KE10 in oil-based formulations. Primers specific for strain KE01 were developed and the RT-PCR was performed as described below:

Primer Design

Primers for the amplification of species-specific *Lactobacillus casei* KE01 (ATCC-PTA3945) set were synthesized (Table 1). All primers were synthesized using the standard desalting processes (Integrated DNA Technologies, Coralville, Iowa). The primer set for strain KE01 was designed by amplification of the 16S rRNA gene of *Lactobacillus* spp., sequenced (City of Hope Research Center, Duarte, Calif.) and compared for base additions, deletions, substitutions, etc. against a public gene bank using Lasergene (DNAStar, Madison, Wis.) software. A primer set for Real-Time PCR was then developed specific for the KE01 strain. This primer set creates a 154 bp fragment. All primer sets were rehydrated to 100 mM with molecular grade water (Eppendorf, Hamburg, Germany) and stored at −20° C. until used.

TABLE 1

| Name | Primer Sequence |
|---|---|
| KE01 F1 (SEQ ID NO 1) | 5'-TTG TCA CCG GCA GTT CTT AC-3' |
| lac upp (SEQ ID NO 2) | 5'-TGT CGT CAG CTC GTG TCG T-3' |

Real-Time PCR

Quantitative real-time PCR on the iCycler iQ was performed in duplicate on 7 µl of template DNA per 25 µl reaction. The iQ supermix reactions consisted of iQ supermix (Bio-Rad, Hercules, Calif.) at a final concentration of 1×, 10 nM fluorescein, SYBR Green I with the supermix master mix (50 mM KCl, 20 mM Tris-HCl, 0.2 mM dNTP, 25 units/ml iTaq DNA Polymerase, 3 mM MgCl$_2$).

Reactions were amplified in a 96-well thin wall PCR plate (Bio-Rad) using the following parameters: 95° C. for 3 min, followed by 40 cycles of denaturation at 95° C. for 10 sec, annealing at 66° C. for 15 sec. Melt curve analysis was performed immediately following amplification by ramping the temperature from 55° C. to 95° C. The presence of a single PCR product was verified both by the presence of a single melting temperature peak representing a specific product (vs. a nonspecific primer-dimer peak) using iCycler iQ analysis software and by detection of a single band of the expected size on a 12.5% TBE-polyacrylamide gel.

Figure 3:
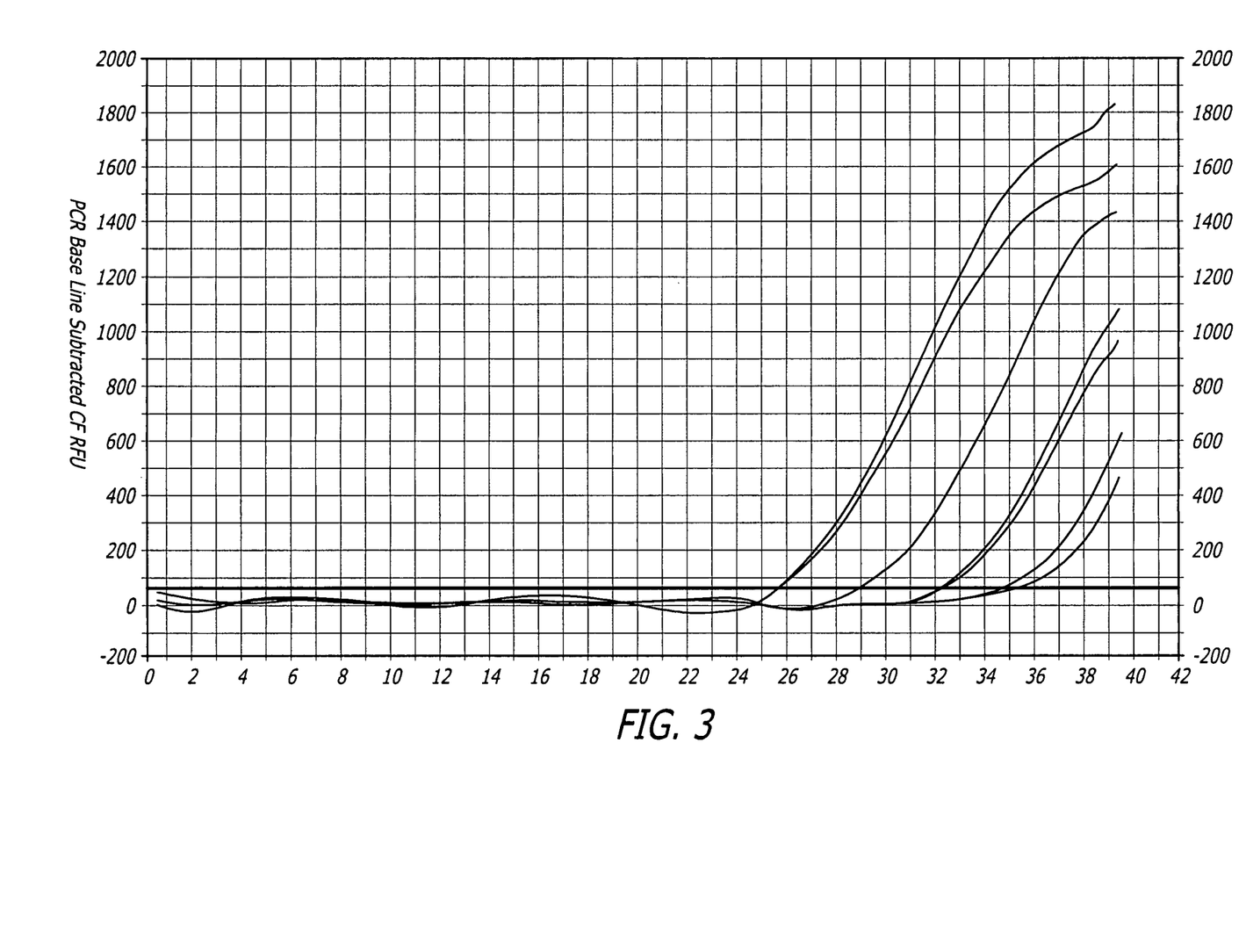
FIG. 3 depicts the standardized real-time PCR used to quantify *lactobaciilus* content of the present invention using KE01 specific primers.
Figure 4:
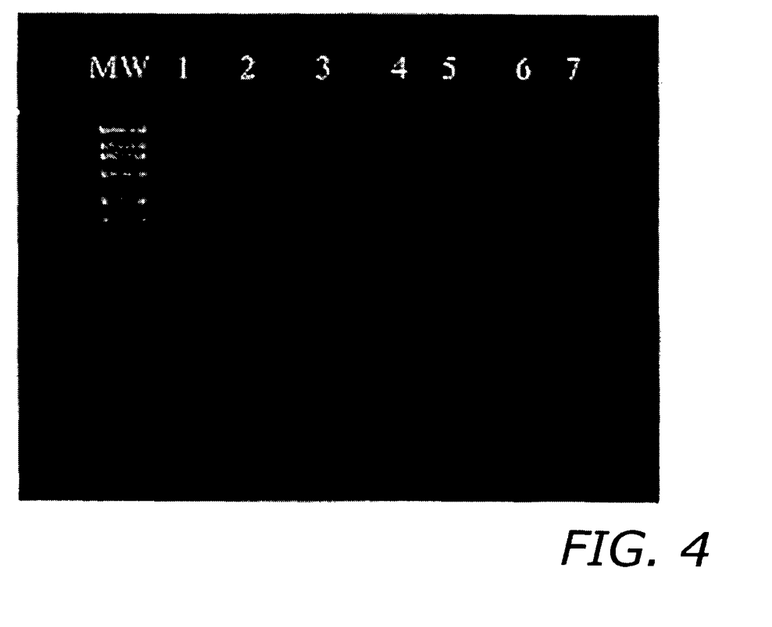
FIG. 4. depicts sodium dodecyl sulfate-polyacrylamide gel electrophoresis (SDS-PAGE) results using the KE01 primers of the present invention.

A standard curve was produced and used to determine the concentrations of the samples. The concentration values were 0.16 ng, 0.016 ng, 0.0016 ng, and 0.00016 ng and used from stock known bacteria (strain KE01). The standard concentration was used from stock *E. coli* (ATCC 43895), and strain KE01. For total *lactobacilli* estimations a mixture of strains, i.e. *L. casei* (ATCC393), *L. pentosus* (ATCC 8041), *L. plantarum* (ATCC 14917), *L. paracasei* subsp. *paracasei* (ATCC 25302) and strain KE01 were used. The DNA of all stock bacteria were extracted and the DNA concentrations were determined by the Picogreen® Quantification kit and diluted accordingly in 1×TE buffer to the appropriate concentrations suitable for RT-PCR analysis. FIG. 3 depicts the results of real-time PCR standards for strain KE01. Each standard concentration (0.16, 0.016, 0.0016, 0.00016 and 0 ng) was run in duplicate (two lines per standard).

DNA Fingerprinting by Random Amplified Polymorphic DNA (RAPD) Assay

The RAPD protocol uses PCR for generating a unique fingerprint for bacterial identification. The analysis by PCR can be performed in a rapid and reliable manner. Accordingly, the RAPD assay has been used for molecular identification and finger printing of strain KE01. A total of 12 *Lactobacillus* spp. type strains from the ATCC collection were fingerprinted and compared with the KE01. For the DNA fingerprinting all the *lactobacillus* strains were cultivated overnight in MRS broth (Difco). The *Lactobacillus* strains analyzed for DNA fingerprint are listed in Table 2.

TABLE 2

| *Lactobacillus* spp. | SOURCE |
|---|---|
| *Lactobacillus* strain KE01 | en-N-tech, Inc., California, USA |
| *Lactobacillus acidophilus* ATCC 4356 | Human [L 917; IFO 13951; NCIB 8690] |
| *Lactobacillus amylovorus* ATCC 33620 | Cattle waste-corn silage |
| *Lactobacillus brevis* ATCC 14869 | Human feces |
| *Lactobacillus casei* subsp. *casei* ATCC 393 | Cheese [IAM 12473; Orland L-323] |
| *Lactobacillus casei* subsp. *rhamnosus* ATCC 7469 | [BUCSAV 227; P. A. Hansen 300; NCDO 243; NCIB 6375; NCTC 6375; NRC 488] |
| *Lactobacillus delbrueckii* subsp. *lactis* ATCC 12315 | Swiss cheese [DSM 20072; IAM 12476; NCDO 1438] |

TABLE 2-continued

| Lactobacillus spp. | SOURCE |
|---|---|
| Lactobacillus fermentum ATCC 14931 | Fermented beets [NCIB 11840] |
| Lactobacillus helvaticus ATCC 15009 | Swiss cheese |
| Lactobacillus paracasei subsp. paracasei ATCC 25302 | [NCDO 151; R094] |
| Lactobacillus pentosus ATCC 8041 | [DSM 20314; NCDO 363; NCIB 8026] |
| Lactobacillus plantarum ATCC 14917 | Pickled cabbage [IAM 124771] |
| Lactobacillus reuteri ATCC 23272 | Human feces |

DNA Extraction Method

DNA was extracted from the *lactobacilli* using the Wizard Genomic DNA Purification Kit (Promega, Madison, Wis.). Briefly, 1 mL of 24-h grown MRS broth culture of each *Lactobacillus* spp. was harvested by centrifugation, cells were resuspended in 50 mM EDTA and treated with 10 mg/mL lysozyme (Sigma, St. Louis, Mo.) at 37° C. for 60 min. *Lactobacilli* cells were pelleted by centrifugation and supernatant was removed. The bacterial pellets were resuspended in the nuclei lysis solution and incubated at 80° C. for 5 minutes. Cell suspension was allowed to cool to room temperature and RNAse was mixed into the solution. The suspension was incubated at 37° C. for 60 min. After incubation, protein precipitation solution was added to the mixture. Solution was mixed on vortex and incubated on ice for 5 min. The mixture was centrifuged for 3 min at 15K×g, supernatant was transferred to a fresh tube and the DNA was precipitated with isopropyl alcohol. The DNA was centrifuged and the isopropyl alcohol was aspirated. The DNA pellet was washed with 70% ethanol and harvested by centrifugation. Ethanol was removed and the pellet was allowed to dry. The DNA was resuspended in tris-EDTA buffer.

PCR Amplification of Extracted DNA

One microliter of the extracted DNA was used in the PCR reactions, which were carried out on the iCycler (Bio-Rad) using a single arbitrary nucleotide sequence according to Cocconcelli, et al. [Cocconcelli, P S et al., Development of RAPD protocol for typing of strains of lactic acid bacteria and entercocci. Lett. Appl. Microbiol. 21:376-9, 1995]. A 2×PCR solution-Premix Taq (Takara, Shiga, Japan) was used for each reaction. Each reaction contained a total volume of 50 µL, 1.25 units of Takara Ex Taq DNA Polymerase, 1× Buffer, 200 µM dNTP Mix (2.5 mM each). Final concentration of the primer was 4 µM, and the primer used for the amplification was 5'-AgCAgCgTgg-3' (Operon Technologies, Inc., Huntsville, Ala.). The reaction mixtures with the template DNA were cycled through the following temperature profile: 1 cycle of 94° C. for 5 min; 40 cycles of 94° C. for 1 min; 29° C. for 1 min; ramp to 72° C. 1.5 min and held at 72° C. for 1.5 min; 1 cycle of 72° C. for 2 min; and held at 4° C.

Gel Electrophoresis

Aliquots of each RAPD amplified reaction (10 µL) were analyzed by 1% (wt/vol) agarose gel electrophoresis in Tris-borate-EDTA buffer according to Sambrook et al. [Sambrook J et al., Molecular Cloning—A Laboratory Manual, 2nd Edition. Cold Spring Harbor Laboratory Press, NY, 1989]. Gels were run for 2 hr at 120V without cooling. The DNA molecular weight marker Hyperladder I (Bioline, Randolph, Mass.) was used as the standard. After electrophoresis the gel was stained with ethidium bromide (5 µg/mL) for 10 min, washed for 5 min and visualized and analysed on a Fluor-S Multilmager (BioRad).

Figure 1:
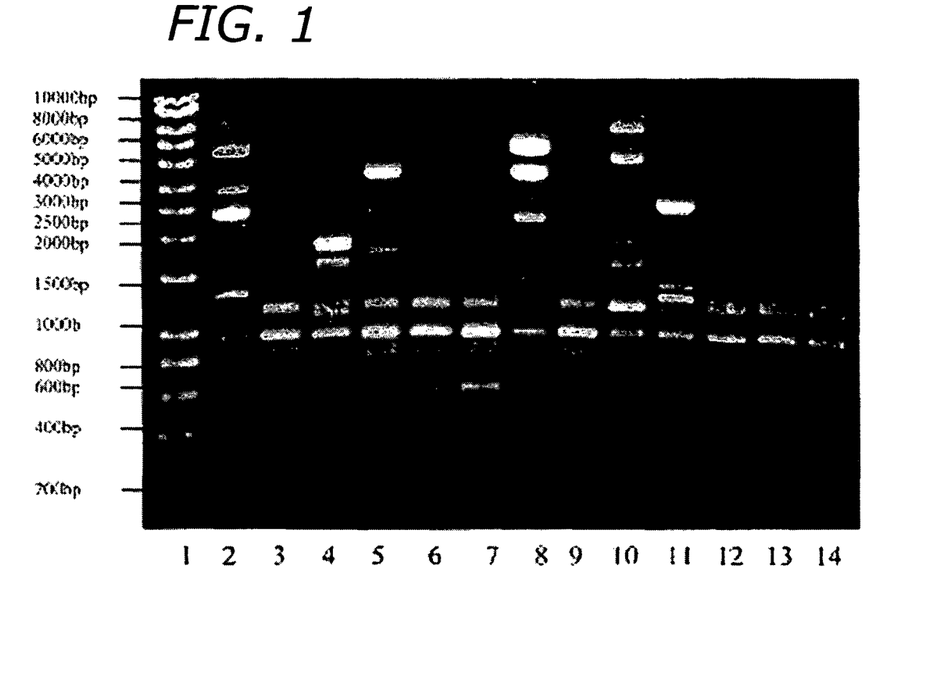
FIG. 1 depicts the genomic fingerprint of *Lactobacillus casei* strain KE01 on 1% agarose gel compared to 12 different *Lactobacillus* type strains based on Randomly Amplified Polymorphic DNA (RAPD) assay.
Figure 2:
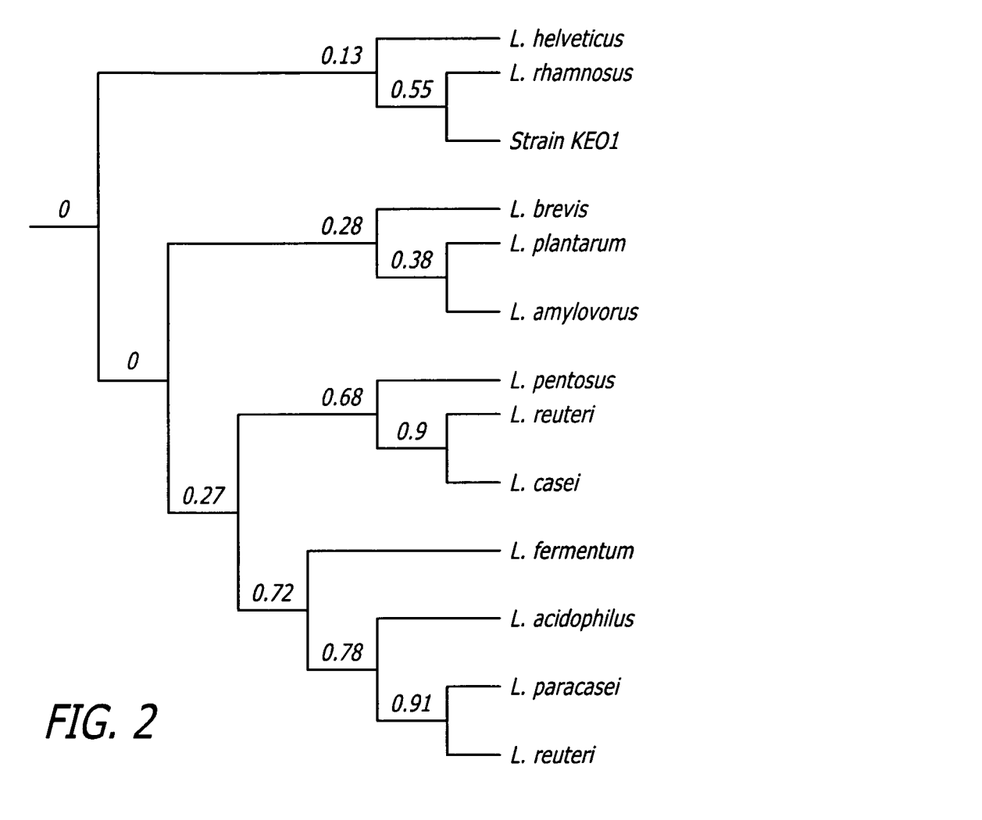
FIG. 2 depicts the phylogenic dendogram deduced from genomic fingerprinting and the relatedness of *Lactobacillus casei* strain KE01 with other species of *Lactobacillus* type strains.

The RAPD assay using a single 10-mer primer produced distinct banding patterns of variable intensities and numbers of amplified products on 1% agarose gel with DNA samples of various *lactobacillus* reference strains and strain KE01. Comparison of the different species fragments on the gel to the reference *Lactobacillus* spp. was noted. The banding pattern with documentation as depicted in FIG. 1 and TABLE 3 serves to uniquely identify strain KE01 and provided a genomic fingerprinting library. Based on the genomic fingerprinting a dendogram was deduced as shown in FIG. 2. Ward's Cluster Method of Phylogenic Analysis was applied. This method minimizes the Sum of Squares of any two clusters that can be formed at each step, creating clusters of small sizes. Based on the phylogenic analysis, strain KE01 showed 13% homology with *Lactobacillus helvaticus* ATCC15009 and 55% homology with *Lactobacillus casei* ssp. rhamnosus ATCC7469.

A pure culture of *Lactobacillus casei* strain KE01 was deposited with the American Type Culture Collection, Bethesda, Md., which was assigned the number ATCC PTA 3945.

The present inventors have demonstrated that by suspending lactic acid bacilli in edible oils, probiotic/prebiotic compositions result having greater viability than previously possible. However, as will be apparent from the examples that follow, merely because a particular oil is edible, and in fact may have health giving qualities of its own, it does not necessarily follow that all edible oils are satisfactory prebiotics. As can be seen in Table 4 below, the percent recovery versus the control ranged from approximately 59% to over 370% during a four week storage. Based on these observation, the present inventors concluded that fish oil, olive oil, rice-bran oil, and soybean oil demonstrate prebiotic effects where the other oils tested were either not prebiotic, or were in fact antibacterial.

TABLE 3

| Lane Number | Band Number | Mol. Wt. (bp) | Identification |
|---|---|---|---|
| 2 | 1 | 4661.359 | Strain KE-01 |
| 2 | 2 | 2986.357 | |
| 2 | 3 | 2457.454 | |
| 2 | 4 | 2255.342 | |
| 2 | 5 | 1565.537 | |
| 2 | 6 | 1354.07 | |
| 2 | 7 | 991.287 | |
| 2 | 8 | 904.264 | |
| 2 | 9 | 596.721 | |
| 3 | 1 | 2457.454 | Lactobacillus acidophilus |
| 3 | 2 | 1231.998 | ATCC# 4356 |
| 3 | 3 | 1003.944 | |
| 3 | 4 | 904.264 | |
| 3 | 5 | 861.774 | |
| 3 | 6 | 617.813 | |
| 4 | 1 | 4721.177 | Lactobacillus amylovorus |
| 4 | 2 | 1969.14 | ATCC# 33620 |
| 4 | 3 | 1894.057 | |
| 4 | 4 | 1725.33 | |
| 4 | 5 | 1672.497 | |
| 4 | 6 | 1271.414 | |
| 4 | 7 | 1203.24 | |
| 4 | 8 | 1023.9 | |
| 5 | 1 | 3611.082 | Lactobacillus brevis |
| 5 | 2 | 3259.978 | ATCC# 14869 |
| 5 | 3 | 2534.42 | |
| 5 | 4 | 2087.693 | |
| 5 | 5 | 1864.831 | |
| 5 | 6 | 1271.414 | |
| 5 | 7 | 1031.994 | |
| 5 | 8 | 940.583 | |
| 5 | 9 | 888.576 | |

TABLE 3-continued

| Lane Number | Band Number | Mol. Wt. (bp) | Identification |
|---|---|---|---|
| 5 | 10 | 651.854 | |
| 6 | 1 | 2545.999 | Lactobacillus delbrueckii |
| 6 | 2 | 1281.464 | ssp. lactis ATCC# 12315 |
| 6 | 3 | 1036.064 | |
| 6 | 4 | 940.583 | |
| 6 | 5 | 892.472 | |
| 6 | 6 | 645.528 | |
| 7 | 1 | 7490.875 | Lactobacillus fermentum |
| 7 | 2 | 2545.999 | ATCC# 14931 |
| 7 | 3 | 1732.051 | |
| 7 | 4 | 1281.464 | |
| 7 | 5 | 1036.064 | |
| 7 | 6 | 953.011 | |
| 7 | 7 | 900.317 | |
| 7 | 8 | 655.041 | |
| 8 | | 14117.898 | Lactobacillus helveticus |
| 8 | | 4936.649 | ATCC# 15009 |
| 8 | | 3634.241 | |
| 8 | | 2776.318 | |
| 8 | | 2394.989 | |
| 8 | | 2105.687 | |
| 8 | | 1529.442 | |
| 8 | | 1036.064 | |
| 9 | 1 | 3588.07 | Lactobacillus paracasei |
| 9 | 2 | 1271.414 | ssp. paracasei |
| 9 | 3 | 1107.771 | ATCC# 25302 |
| 9 | 4 | 1027.939 | |
| 9 | 5 | 932.388 | |
| 9 | 6 | 892.472 | |
| 9 | 7 | 636.154 | |
| 10 | 1 | 6200.546 | Lactobacillus plantarum |
| 10 | 2 | 4968.224 | ATCC# 14917 |
| 10 | 3 | 4263.326 | |
| 10 | 4 | 1969.14 | |
| 10 | 5 | 1685.552 | |
| 10 | 6 | 1322.462 | |
| 10 | 7 | 1231.998 | |
| 10 | 8 | 1027.939 | |
| 10 | 9 | 223.284 | |
| 11 | 1 | 2592.843 | Lactobacillus casei ssp. |
| 11 | 2 | 2324.117 | rhamnosus ATCC# 7469 |
| 11 | 3 | 1685.552 | |
| 11 | 4 | 1430.79 | |
| 11 | 5 | 1312.091 | |
| 11 | 6 | 1212.751 | |
| 11 | 7 | 1011.88 | |
| 11 | 8 | 780.732 | |
| 12 | 1 | 9035.455 | Lactobacillus pentosus |
| 12 | 2 | 6787.29 | ATCC# 8041 |
| 12 | 3 | 2405.288 | |
| 12 | 4 | 2198.014 | |
| 12 | 5 | 1453.497 | |
| 12 | 6 | 1261.443 | |
| 12 | 7 | 1198.513 | |
| 12 | 8 | 982.651 | |
| 12 | 9 | 667.942 | |
| 13 | 1 | 2945.799 | Lactobacillus casei ssp. |
| 13 | 2 | 2374.522 | casei ATCC# 393 |
| 13 | 3 | 2169.899 | |
| 13 | 4 | 1436.433 | |
| 13 | 5 | 1217.534 | |
| 13 | 6 | 974.089 | |
| 13 | 7 | 876.989 | |
| 13 | 8 | 839.445 | |
| 13 | 9 | 661.46 | |
| 13 | 10 | 583.785 | |
| 14 | 1 | 2324.117 | Lactobacillus reuteri |
| 14 | 2 | 2114.743 | ATCC# 23272 |
| 14 | 3 | 1402.903 | |
| 14 | 4 | 1184.442 | |
| 14 | 5 | 944.708 | |
| 14 | 6 | 832.131 | |
| 14 | 7 | 639.264 | |

As discussed above, the present inventors have discovered that selecting the proper prebiotic oil provides a means for preserving and enriching the viability and hence probiotic activity of the Lactobacilli preparations of the present invention. (Note, non-viable Lactobacilli may also possess probiotic effects, however, non-viable preparations may not benefit significantly from the prebiotic formulations of the present invention.) However, when the optimum prebiotic oil is combined with an optimized delivery system, overall probiotic activity can be increased and/or preserved over a longer time period.

Figure 5:
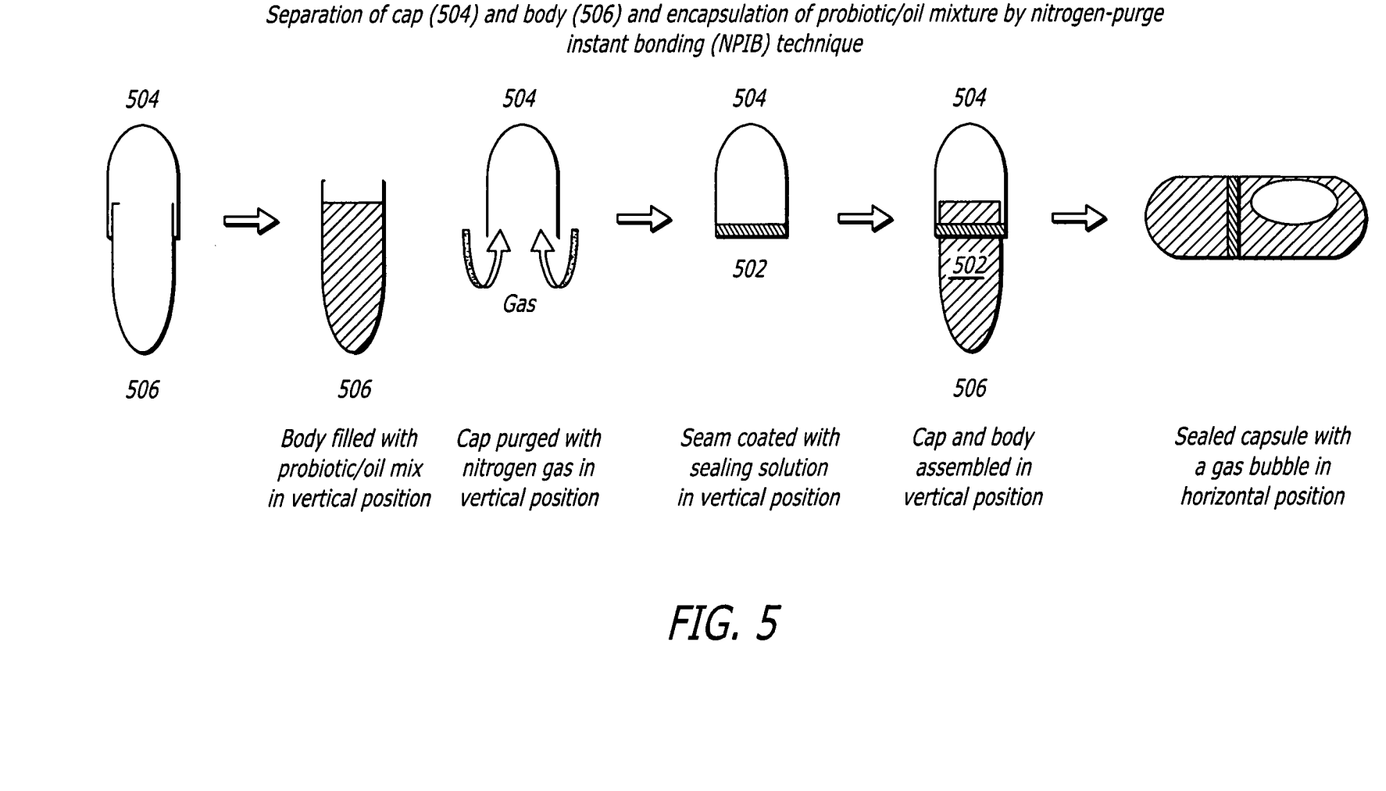
FIG. 5 depicts the process for making the anaerobic encapsulation system using NPIB in accordance with the teachings of the present invention.

Probiotic lactobacilli require anaerobic or microaerophilic conditions for optimum viability. Though oil immersion provides low water activity and limited oxygen diffusion, any evacuation of oxygen from the microenvironment would enhance the probiotic preservation. Accordingly, a novel anaerobic encapsulation system using nitrogen-purge-instant-bonding (NPIB) as depicted in FIG. 5 has been developed to protect the oil-emulsified probiotic formulations of the present invention. This process provides an optimal microenvironment anaerobic/microaerophilic) condition ideal for the probiotic bacteria. As used herein, the term "anaerobic" will mean a low oxygen tension environment and includes a strict anaerobic environment and microaerophilic environments. The NPIB system of the present invention provides for oxygen displacement simultaneously with sealing the oil emulsified lactobacilli in a hard, two-piece capsule.

Moreover, the NPIB system of the present invention may also be used with other compositions including, but not limited to powders, oil-based liquids, oil-based suspensions, oil-based pastes, waxes, low-water content emulsions and a variety of bioactive compounds including, but not limited to lactoferrin. Moreover, the choice of capsular material is highly flexible. For example in one embodiment of the present invention natural two piece hard gelatin/vegetable capsules are used, in another embodiment soft gelatin/vegetable capsules are used, additional capsule compositions included assorted synthetic and natural polymers. The NPIB system of the present invention can be incorporated into any type of capsule filling equipment, including the manual, semi or fully automated as well as continuous or intermittent motion devices.

FIG. 5 depicts the process for making the anaerobic encapsulation system of the present invention. After separation of cap and body (504 and 506 respectively in FIG. 5), the oil-based bioactive composition of the present invention is added to the capsule body 506. Next, an anaerobic gas such as but not limited nitrogen or argon is injected into the capsule cap 504 and a sealing solution is applied to the inner, lower section of the cap (seam 502). This results in instant bonding of the cap 504 and body 506 at the time when cap and body are joined during the closing step. In one embodiment the sealing solution is an aqueous-alcohol solution comprising from approximately 50% to 99% ethanol, 90% being preferred (for vegetable capsules) or 10% to 70% isopropyl alcohol (IPA), 60% being preferred (for gelatin capsules) and 15%-30% IPA being optimum for vegetable-based capsules. However, those skilled in the art of formulation and filling technologies understand that other organic solvents are suitable and combinations of different solvents may be used. For example, and not intended as a limitation, vegetable capsules comprising plant-derived celluloses are soluble at varying degrees in ethanol, isopropyl alcohol or water. The specific ratio of these three solvents in a sealant is dependant on several factors such as (i) rate of sealant application, (ii) volume of sealant applied, (iii) method of sealant application, (iv) degree of sealant atomization, (v) method of atomization, and (vi) residence time. These factors are also strictly dependant on the wet-ability, solubility and softening properties of the capsular materials. Accordingly, the following conditions should be controlled during the sealing process: (a) the softening should not exceed the structural rigidity of the cap during the closing step. Beyond a certain limit, the cap deforms and fails to hold to the body; (b) the wet-ability and solubility properties of the cap should be retained and effectively transferred to the body. This would allow proper fusion of the inner surface of the cap with the outer surface of the body during the closing step; (c) The cap and head should have excellent closure compatibility, since ethanol and isopropyl alcohol evaporate rapidly, while water evaporates slowly over a period of few hours; (d) the wet-ability and solubility properties are highly critical during instant bonding process.

In one embodiment of the present invention the nitrogen purge and sealing steps are done while the capsule is in a vertical position FIG. 5. This differs from prior art procedures that fill and close the capsules in the vertical position and then immediately ejected the filled capsule into the horizontal position. This changed orientation (from vertical to horizontal) causes the capsule's fluid contents migrate into capsule seam 502 between the capsule halves 504 and 506. Once the capsule seam is contaminated with fluid, the sealing step is considerably less efficient resulting in leakage of product from the capsule and contamination of the capsule contents with air.

The NPIB system of the present invention effectively solves this problem by sealing the capsule immediately after filling and purging before any change in capsule potion is initiated. Consequently, the capsule seam remains uncontaminated and the seal integrity uncompromised.

In one embodiment of the present invention a method for making a probiotic composition is provided comprising emulsifying a Lactic Acid Bacteria (LAB) in an edible oil, the edible oil having prebiotic properties. Next a hard capsule body 506 is filled with the emulsified probiotic while the capsule is in the vertical orientation. The filled capsule body 506 remaining in the vertical orientation. Next the cap 504 is purged with a noble gas such as, but not limited to nitrogen or argon and a sealing solution is applied to the cap seam 502. Following application for the sealant to the cap seam 502, the cap 504 and capsule body 506 are brought together and instantly bonded. In some embodiments bone-dry carbon dioxide gas may be used as well. Finally the filled, purged capsule is sealed with an aqueous-organic solvent solution. It is understood by those skilled in the art of formulation and filling that the purging process can be done contemporaneously with the filling process.

The following examples are meant to be non-limiting in their scope. To the extent specific ranges, compositions, ingredients and conditions are called out these are to be considered merely exemplary for the purposes of teaching preferred embodiments and or best mode.

EXAMPLES

Example 1

Preparation and Testing of Prebiotic Oils

A pure culture of *Lactobacillus casei* strain KE01 is revived in a fermentation broth media containing proteins, vitamins, minerals and carbohydrate source. A seed culture is prepared in a fermentor attached to fermentation vessel. Microbial purity is monitored at defined time points (through log phase and end cycle) during the fermentation process. The microbial mass is harvested in a sanitized separator and the slurry of cell concentrate was freeze-dried after mixing with carriers and cryoprotectants. The freeze-dried *lactobacillus* cell concentrate was milled to fine powder using sanitized milling equipment. The quality of *lactobacilli* powder was assured for purity and viability prior to use. The viability was about $10^{10}$ CFU *lactobacilli*/gm of powder.

The probiotic *lactobacilli* powder is then thoroughly mixed with different oils listed in Table 4 to a final 0.1% emulsion (about 0.1 g powder containing $10^9$ CFU *lactobacilli* mixed in 1 mL oil). In one embodiment of the present invention the emulsion is prepared in 10 mL sterile glass tubes and homogenized in a vortex blender. The blended mixture is then and sealed with air tights caps before testing. Multiple tubes for each type of oil emulsion were prepared, and the tubes were stored at room temperature (28° C.). Tubes containing $10^9$ CFU *lactobacilli* powder without any oil served as growth controls.

At weekly intervals for four weeks a 1 mL sample of each oil containing *L. casei* was tested for viability as follows: nine mL of sterile deMann Rogosa Sharpe (MRS) broth was added to each test aliquot and the contents were homogenized using a vortex blender. Serial ten-fold dilutions of the homogenized mixture were prepared in MRS broth tubes. All tubes were incubated at 37° C. for 18 hours. *Lactobacilli* growth was measured as change in optical density at 600 nm at the lowest dilution. The growth of control tubes, measured as optical density at 600 nm at similar dilution, was considered 100%. The test results were expressed as percent viability as compared to the Controls (Table 4).

*Lactobacilli* acclimatized to oil environment within the first week following emulsification. In subsequent weeks, however, the viability of *lactobacilli* gradually diminished in certain oils i.e. hazelnut, primrose, pumpkin and terila, suggesting a low probiotic recovery. In contrast, fish oil (omega), olive oil (extra-virgin), rice-bran oil, and soybean oil all provided an excellent recovery of *lactobacilli*. Moreover, based on the results expressed in Table 4 below, the present inventors have reasoned that flax seed oil and vitamin E oil may also demonstrate similar prebiotic activity.

TABLE 4

Recovery of *Lactobacilli* from selected oils in MRS broth (37 .degree. C.).

| Oil-emulsion Type | $1^{st}$ week | $2^{nd}$ week | $3^{rd}$ week | $4^{th}$ week |
|---|---|---|---|---|
| Fish (Omega) | 122% | 220% | 255% | 280% |
| Hazelnut | 92% | 88% | 67% | 59% |
| Olive (Extra virgin) | 195% | 314% | 379% | 374% |
| Primrose | 87% | 87% | 94% | 95% |
| Pumpkin | 79% | 78% | 82% | 85% |
| Rice-bran | 108% | 212% | 223% | 267% |
| Soybean | 112% | 217% | 274% | 290% |
| Terila (pure) | 96% | 97% | 88% | 77% |

Note:
Controls i.e. *Lactobacilli* stored under similar conditions and when revived in MRS considered as 100% when compared to the test samples.

Example 2

Preparation of Probiotic Samples in Nitrogen Purged Instantly Bonded Capsules and Testing Each gelatin/vegetable capsule prepared by the NPIB system contained about 550 mg emulsion comprising of $10^9$ CFU of *lactobacilli* and 0.5 ml of fish oil (Omega), olive, rice-bran or soybean oil. Ten capsules of each oil-emulsified *lactobacilli* were kept in several glass storage bottles with air-tight caps and stored at room (28° C.) or refrigerated (4°

C.) temperatures. Bottles of each oil-emulsion type were taken from both storage conditions, periodically, each month, and the capsular contents were tested for viability of *lactobacilli* (colony forming units, CFU). Capsules made with NPIB system containing $10^9$ CFU *lactobacilli* without any oil served as controls.

Each gelatin/vegetable capsule was allowed to dissolve in test tubes containing 10 mL MRS broth for about 30 minutes at room temperature. After release of the capsular contents, tubes were thoroughly homogenized using a vortex blender. Serial 10 fold dilutions of the homogenized mixture were prepared in MRS broth tubes. All tubes were incubated at 37° C. for 18 h. The growth of control tubes, measured as optical density at 600 nm at similar dilutions, was considered 100%. Real-time PCR was also used to determine the purity of the revived strain KE01 from the encapsulated oil-mixtures and the total *lactobacillus* mass. The test results were expressed as % viability as compared to the Controls (Table 5).

All four types of oil-emulsified probiotic *lactobacilli* demonstrated a significant recovery rate ranging from 400% to 760% over a period of twelve-month storage at room temperature. These data compared to the 100% revival rate of control *lactobacilli* suggested a potent prebiotic effect for these oil-emulsion types.

TABLE 5

Percent viability of oil-emulsified *lactobacilli* (in capsules prepared by the NPIB system) stored at room (28° C.) temperatures for months and revived in MRS broth (37° C.)

| Oil-emulsion Type (NPIB-System) | Stored at room temp. (28° C.) | | | | |
|---|---|---|---|---|---|
| | $2^{nd}$ month | $3^{rd}$ month | $4^{th}$ month | $5^{th}$ month | $6^{th}$ month |
| Fish (Omega) | 565% | 568% | 572% | 525% | 482% |
| Olive (Extra-virgin) | 735% | 763% | 759% | 683% | 403% |
| Rice-bran | 484% | 439% | 448% | 382% | 267% |
| Soybean | 411% | 409% | 401% | 289% | 230% |

Note:
Controls i.e. *Lactobacilli* encapsulated using NPIB system, stored under similar conditions and when revived in MRS considered as 100% compared to the test samples.

Furthermore, the KE01 cells revived from encapsulated oil-mixtures were tested for purity and probiotic activity compared to their stock cultures. *Lactobacilli* revived from the oil-mixtures showed a high degree of purity, with a 100% identity match with strain KE01 according to real-time PCR analysis. These revived *lactobacilli* demonstrated probiotic profiles, i.e. ammonia/sulfide reduction in vitro, intestinal Caco-2 cell adhesion, and competitive exclusion of enteric pathogens from Caco-2 monolayers, similar to their KE01 stock culture. These data suggested that encapsulation of KE01 in specified oil mixtures with NPIB system did not affect or alter the probiotic activity of this *lactobacillus* upon revival over extend periods of time.

Storage of oil-emulsified probiotic formulations at room temperature is user-friendly and commercially preferred. Such storage condition could free the probiotic product from any refrigeration and without compromising viability of the probiotic. Furthermore, the prebiotic enhancement of cellular revival suggested a potent functional activity of the oil-emulsified probiotic encapsulations.

Additional variations considered within the scope of the present invention include the addition of viscosity enhancers to the encapsulated contents and extra-capsular coatings. For example, viscosity enhancers such as glycerols (eg. glycerine); glycols (e.g., polyethylene glycols, propylene glycols); plant-derived waxes (e.g., carnauba, rice, candililla), non-plant waxes (beeswax); emulsifiers (e.g., lecithin); and silicas (e.g., silicon dioxide) are compatible ingredients for NPIB technology. These viscosity enhancers could provide uniform dispersion of the capsular contents and also could improve microaerophilic/anaerobic conditions for the probiotic organism in the encapsulation.

Extra-capsular coatings serve various applications including taste masking, delayed release, vapor/gas diffusion barrier, flavor, color, aroma, enteric protection and leak safety. Such coatings include but are not limited to celluloses (e.g., methyl- and ethyl-celluloses); methacrylates; and shellacs (e.g., pharmaceutical glazes), just to name a few.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference.

I claim:

1. A method for anaerobic encapsulation of a composition comprising:
   filling a capsule body with a composition while said capsule body is in a vertical orientation;
   purging a capsule cap with an anaerobic gas by injecting said anaerobic gas into said capsule cap;
   applying a sealing solution to said capsule cap before securing said capsule cap to said capsule body while said capsule body is in said vertical orientation; and
   securing said capsule cap onto said capsule body in said vertical orientation to produce an instant bonding of said capsule cap to said capsule body at the time when the capsule cap and capsule body are joined, thereby anaerobically encapsulating said composition within a capsule formed by said instant bonding of said capsule cap to said capsule body.

2. The method according to claim 1 wherein said capsule body and said capsule cap comprise materials derived from a group consisting of vegetables, animal gelatin, synthetic polymers and natural polymers.

3. The method according to claim 1 wherein said gas is selected from a group consisting of nitrogen, argon and carbon dioxide.

4. The method according to claim 1 wherein said sealing solution comprises an organic solvent selected from the group consisting of isopropyl alcohol and ethanol.

5. The method of claim 1 wherein said composition further comprises an oil-emulsified probiotic formulation whose preservation is enhanced by said purging with said anaerobic gas.

6. The method of claim 5 whereby said composition further comprises a probiotic formulation derived from *Lactobacillus casei* combined with at least one prebiotic oil.

7. A method for anaerobically encapsulating a probiotic composition comprising:
   filling a capsule body with a composition comprising lactic acid bacteria combined with at least one prebiotic oil said capsule body held in a vertical orientation;
   purging a capsule cap with nitrogen gas while holding said capsule cap in said vertical orientation;
   applying an organic solvent sealing solution to the inside of said capsule cap before securing said capsule cap to said capsule body, while holding said capsule cap in said vertical orientation; and
   securing said capsule cap onto said capsule body, both in said vertical orientation, said capsule cap instantly bonding to said capsule body at the time when said capsule cap and said capsule body are joined, thereby anaerobically encapsulating said composition within a capsule formed by said instant bonding of said capsule cap to said capsule body.

8. The method according to claim 7 wherein said capsule body and said capsule cap comprise materials derived from a group consisting of vegetables, animal gelatin, synthetic polymers and natural polymers.

* * * * *